United States Patent
Papp et al.

(10) Patent No.: US 10,315,182 B2
(45) Date of Patent: Jun. 11, 2019

(54) CYLINDRICAL REACTOR AND USE THEREOF FOR CONTINUOUS HYDROFORMYLATION

(71) Applicant: BASF SE, Ludwigshafen am Rhein (DE)

(72) Inventors: Rainer Papp, Speyer (DE); Oliver Christian Gobin, München (DE); Oliver Bey, Niederkirchen (DE); Jens Rudolph, Abu Dhabi (AE); Hans-Günter Thelen, Mannheim (DE)

(73) Assignee: BASF SE, Ludwigshafen Am Rhein (DE)

( * ) Notice: Subject to any disclaimer, the term of this patent is extended or adjusted under 35 U.S.C. 154(b) by 0 days.

(21) Appl. No.: 16/064,756

(22) PCT Filed: Dec. 21, 2016

(86) PCT No.: PCT/EP2016/082057
§ 371 (c)(1),
(2) Date: Jun. 21, 2018

(87) PCT Pub. No.: WO2017/108878
PCT Pub. Date: Jun. 29, 2017

(65) Prior Publication Data
US 2019/0001298 A1 Jan. 3, 2019

(30) Foreign Application Priority Data

Dec. 22, 2015 (EP) .................................... 15202114

(51) Int. Cl.
*C07C 45/50* (2006.01)
*B01J 10/00* (2006.01)
(Continued)

(52) U.S. Cl.
CPC ........... *B01J 19/246* (2013.01); *B01J 10/002* (2013.01); *B01J 19/006* (2013.01); *C07C 45/50* (2013.01); *B01J 2219/00078* (2013.01)

(58) Field of Classification Search
CPC ............ C07C 45/50; B01J 10/00; B01J 19/24
(Continued)

(56) References Cited

U.S. PATENT DOCUMENTS

| 3,830,846 A | 8/1974 | Duembgen et al. |
| 5,849,972 A | 12/1998 | Vicari et al. |

(Continued)

FOREIGN PATENT DOCUMENTS

| DE | 1135879 B | 9/1962 |
| DE | 1205514 B | 11/1965 |

(Continued)

OTHER PUBLICATIONS

International Search Report for PCT/EP2016/082057 dated Mar. 17, 2017.
(Continued)

*Primary Examiner* — Huy Tram Nguyen
(74) *Attorney, Agent, or Firm* — Drinker Biddle & Reath LLP

(57) ABSTRACT

Proposed is a cylindrical reactor (1) having a vertical longitudinal axis for continuous hydroformylation of a $C_6$-$C_{20}$-olefin or a mixture of $C_6$-$C_{20}$-olefins with synthesis gas in the presence of a homogeneously dissolved metal carbonyl complex catalyst,
having a multiplicity of Field tubes (2) which are oriented parallel to the longitudinal axis of the reactor (1) and welded into a tube plate at the upper end of the reactor (1),
having a circulation tube (3) open at both ends which envelops the Field tubes (2) and at its lower end projects beyond said tubes,
(Continued)

having a jet nozzle (4) at the bottom of the reactor (1) for injecting the reactant mixture comprising the $C_6$-$C_{20}$-olefin, the synthesis gas and the metal carbonyl complex catalyst, wherein the Field tubes (2) are configured in terms of their number and their dimensions such that the total heat exchanger area of said tubes per unit internal volume of the reactor is in the range from $1~m^2/m^3$ to $11~m^2/m^3$ and the cross sectional area occupied by the Field tubes (2) per unit cross sectional area of the circulation tube (3) is in the range from $0.03~m^2/m^2$ to $0.30~m^2/m^2$, a gas distributor ring (5) is provided at the lower end of the circulation tube (3), at the inner wall thereof, via which a substream of the synthesis gas is feedable, and wherein one or more distributor trays (6) are provided in the circulation tube (3).

11 Claims, 4 Drawing Sheets

(51) Int. Cl.
*B01J 19/24* (2006.01)
*B01J 19/00* (2006.01)

(58) Field of Classification Search
USPC .......................................................... 422/198
See application file for complete search history.

(56) References Cited

U.S. PATENT DOCUMENTS

| | | | |
|---|---|---|---|
| 6,444,856 B2 | 9/2002 | Grenacher et al. | |
| 6,642,420 B1 | 11/2003 | Zehner et al. | |
| 6,723,884 B1 | 4/2004 | Grenacher et al. | |
| 6,838,061 B1 * | 1/2005 | Berg | B01J 8/226 422/198 |
| 2011/0144391 A1 * | 6/2011 | Becker | B01J 4/002 568/420 |
| 2016/0265084 A1 | 9/2016 | Rudolph et al. | |

FOREIGN PATENT DOCUMENTS

| | | |
|---|---|---|
| DE | 1938104 A1 | 2/1971 |
| DE | 1938102 A1 | 3/1972 |
| DE | 19836807 A1 | 2/2000 |
| DE | 19854637 A1 | 5/2000 |
| DE | 10126363 A1 | 12/2001 |
| EP | 2043774 A2 | 4/2009 |
| GB | 1079209 A | 8/1967 |
| GB | 1308206 A | 2/1973 |
| WO | WO-9514647 A1 | 6/1995 |
| WO | WO-0114297 A1 | 3/2001 |
| WO | WO-2008051301 A2 | 5/2008 |
| WO | WO-2015018710 A1 | 2/2015 |

OTHER PUBLICATIONS

Written Opinion of the International Searching Authority for PCT/EP2016/082057 dated Mar. 17, 2017.

* cited by examiner

CYLINDRICAL REACTOR AND USE THEREOF FOR CONTINUOUS HYDROFORMYLATION

CROSS-REFERENCE TO RELATED APPLICATIONS

This application is a national stage application (under 35 U.S.C. § 371) of PCT/EP2016/082057, filed Dec. 21, 2016, which claims benefit of European Application No. 15202114.3, filed Dec. 22, 2015, both of which are incorporated herein by reference in their entirety.

BACKGROUND OF THE INVENTION

The present invention relates to a cylindrical reactor suitable for exothermic heterogeneous reactions comprising injection of a gaseous reactant and a liquid reactant and especially for hydroformylation reactions. The invention further relates to a continuous process for producing aldehydes and/or alcohols having 6 to 20 carbon atoms by hydroformylation of olefins with synthesis gas in the presence of a transition metal catalyst homogeneously dissolved in the liquid reaction medium in such a reactor.

PRIOR ART

Hydroformylation or oxo synthesis is an important large industrial scale process used for producing aldehydes from olefins and synthesis gas, i.e. a mixture of carbon monoxide and hydrogen. The aldehydes obtained may optionally be hydrogenated with hydrogen to afford the corresponding alcohols in the same operation or subsequently in a separate hydrogenation step. The process is generally performed under homogeneous catalysis, a transition metal catalyst dissolved in the liquid phase of the reaction mixture being employed. Those skilled in the art have a wide selection of proven oxo synthesis processes at their disposal (cf. J. Falbe, editor, "New Syntheses with Carbon Monoxide", Springer-Verlag, New York 1980, pp 162-174). While lower olefins are now hydroformylated almost exclusively with ligand-modified rhodium or cobalt catalysts, for example with phosphine-modified rhodium catalysts, oxo synthesis with unmodified cobalt or rhodium catalysts still dominates in the reaction of higher olefins (i.e. of olefins having more than 6 carbon atoms). The term unmodified catalysts is to be understood as meaning catalysts which, other than CO and $H_2$, comprise no further ligands, especially organophosphoryl compounds (for example triphenylphosphine).

With the exception of the unbranched olefins where retaining the linear structure during hydroformylation is of great importance for the end products, the branched olefins readily obtainable by oligomerization of $C_3$- and/or $C_4$-olefins are hydroformylated on a large industrial scale almost exclusively with unmodified cobalt carbonyls, i.e. in the absence of additional organic, phosphorus-containing ligands. This catalyst system is not only very cost-effective but also universally employable. In addition, starting from the same relatively long-chain starting olefins, higher yields of the particularly coveted linear aldehydes are obtained with unmodified cobalt catalysts than with unmodified rhodium catalysts.

The reaction of olefins with carbon monoxide and hydrogen to afford aldehydes and alcohols is exothermic. Continuous performance of this reaction on a large industrial scale thus requires that precautions be taken to ensure that the heat of reaction is distributed uniformly in the reaction mixture and removed. Local temperature peaks which result in undesired side reactions and consecutive reactions need to be largely avoided. It is also necessary to ensure thorough commixing of the liquid and gaseous starting materials so that the reaction proceeds with the highest possible conversion.

The processes used on a large industrial scale at present are distinguished essentially by the form in which the cobalt catalyst is made available to the hydroformylation reactor and by the way in which after hydroformylation the catalyst is removed from the reaction mixture and, with the smallest possible losses, recycled back into the process.

One proven method is the use of aqueous solutions of cobalt salts of lower carboxylic acids, preferably cobalt formate or cobalt acetate. Under the conditions prevailing in the reactor, the Co(II) salts are rapidly converted into the actual hydroformylation catalyst, namely cobalt carbonyl hydride ($HCo(CO)_4$). The hydroformylation is effected in a high-pressure reactor containing an intimate mixture of olefin, catalyst complex and synthesis gas at elevated temperatures, for example from 120° C. to 210° C., and elevated pressures, for example from 100 to 400 bar. After reaction of the olefin the cobalt carbonyls previously homogeneously dissolved in the organic phase can be converted back into Co(II) compounds by a valence change on the central atom using oxidizing substances, The Co(II) compounds are extracted from the organic reaction product using a weakly acidic, aqueous phase, so that after phase separation the organic reaction product is virtually cobalt-free and may be sent directly for further processing.

The problem here is that, as a function of cobalt concentration and temperature, the catalytic cobalt carbonyl hydride is stable only above a respective particular carbon monoxide partial pressure below which it precipitates as metallic cobalt which is deposited in the reactor and results in catalyst losses and in blockages, in particular in pipes and fittings. A stability diagram of cobalt carbonyl hydride as a function of the variables temperature and carbon monoxide partial pressure is reproduced in the monograph by J. Falbe (editor): "New Synthesis with Carbon Monoxide", Springer Verlag, Berlin, 1980, p. 17, fig. 1.9.

Large industrial scale hydroformylation processes must therefore not only ensure the most uniform possible commixing of the reactants, i.e. of the organic, liquid olefin phase, of the gaseous phase comprising carbon monoxide and hydrogen and possibly of the aqueous cobalt-containing catalyst solution, and also uniform distribution and rapid removal of the heat of reaction but must also ensure that the cobalt catalyst is substantially homogeneously distributed over the reaction zone in the active form as cobalt carbonyl hydride.

A process for removing the heat of reaction via an external heat exchanger which is often utilized in industry cannot meet the above requirements since active catalyst would precipitate in the external circuit on account of the relatively low carbon monoxide partial pressure there prevailing.

A great many processes have therefore been developed which ensure removal of the heat of reaction inside the hydroformylation reactor.

DE 1 135 879 describes that the interior of the reactor may contain a freestanding circulation tube which brings about a circulating convection flow. The interior of the reactor may also be provided with cooling tubes in which the heat of reaction can be harnessed for steam generation. The reaction and process parameters are described in detail unlike the further construction of the reactor.

Document DE 1 205 514 describes passing at least the liquid reaction participants into the reactor at high speed, in particular via injection nozzles.

DE 1 938 102 discloses circulation apparatuses comprising a vertical high-pressure reactor comprising a mixing zone or bundles of mixing zones of different diameters and the introduction of reaction participants with a nozzle or a bundle of nozzles into the reaction zone. The mixing zone may in particular be a cylindrical tube or cone segment and the nozzle a slot or annular nozzle. This document also describes that organic substances or water may be employed as cooling liquid. The boiling point is influenced by the pressure employed. The cooling zone is fed with sufficient liquid to ensure that the heat transfer surfaces are always wetted. It is preferable when a temperature difference between the coolant and the reactor contents of from 20° C. to 100° C. is employed. The arrangement of Field tubes and/or further devices inside the vertical high-pressure reactor is not described.

DE 1 938 104 describes a vertical high-pressure reactor with a circulation tube and injection via a multimaterial nozzle. The oxo reactor has a cooling system having an average area of 190 m$^2$, the cooling system being operated with methanol. The arrangement of Field tubes and/or further devices inside the vertical high-pressure reactor is not known.

DE 198 54 637 describes a reactor of tall cylindrical construction comprising a downward-directed jet nozzle disposed in the upper region of the reactor, wherein a guide tube is concentrically arranged over the entire length inside the reactor. In one embodiment there is a baffle plate on the side of the guide tube facing away from the jet nozzle. Outside the guide tube there may be heat exchangers, in particular Field tube heat exchangers, in the annular space. A process for continuous performance of gas-liquid and liquid-liquid reactions is described. The feed flow direction into the reactor is in the direction of gravity and no arrangement of Field tubes in the guide tube of the reactor is described.

DE 101 26 363 describes a hydroformylation reactor having a nozzle with an adjustable flow cross section but shows no devices for heat removal. The adjustable nozzle makes it possible to alter energy input. This makes it possible to adapt said input to the load at which a plant is run. The vertical high pressure tube may have one or more internals arranged in it which define one or more mixing zones. A guide tube and/or an arrangement of Field tubes inside the guide tube of the reactor is not described.

EP 2 043 774 describes a hydroformylation reactor with internal cooling by means of Field tubes arranged circularly in the reactor longitudinal direction and firmly joined to one another by means of metal plates such that they form a circulation tube. This construction suffers from the following disadvantages in particular:

Complex fabrication and repair and low flexibility since the number of tubes and thus the heat transfer area are limited and the width of the outer annular space between the circulation tube and the reactor inner shell cannot be easily adjusted.

Known tubular reactors for hydroformylation of olefins have the particular disadvantages of limited heat transfer area, low variability in the adjustment of heat transfer area, low throughflow rates, backflows in the guide tubes of the reactors and consequential precipitation of catalysts and the disadvantage of complex fabrication and repair.

It is accordingly an object of the present invention to provide an improved reactor having a central tube insert for hydroformylation of olefins which is stable in operation and does not exhibit the abovementioned disadvantages. In particular, fluid backflow inside the tube insert and precipitation of the catalyst are to be avoided. Moreover, sufficient heat transfer area in the tubular reactor is to be provided and a high commixing of the reactants is to be ensured.

The object is achieved by a cylindrical reactor having a vertical longitudinal axis,
    having a multiplicity of Field tubes which are oriented parallel to the longitudinal axis of the reactor and affixed to the upper end of the reactor,
    having a tube insert open at both ends which envelops the Field tubes and at its lower end projects beyond said tubes,
    having an inlet nozzle or a plurality of inlet nozzles at the bottom of the reactor for injecting a reactant mixture comprising at least one gaseous component and at least one liquid component, wherein
    the Field tubes are configured in terms of their number and their dimensions such that
    the total heat transfer area of said tubes per unit internal volume of the reactor is in the range from 1 m$^2$/m$^3$ to 12 m$^2$/m$^3$ and
    the cross sectional area occupied by the Field tubes per unit cross sectional area of the tube insert is in the range from 0.03 m$^2$/m$^2$ to 0.30 m$^2$/m$^2$.

The invention further provides a continuous process for producing $C_7$-$C_{21}$-oxo products by hydroformylation of at least one $C_6$-$C_{20}$-olefin with synthesis gas in the presence of a homogeneously dissolved transition metal catalyst, wherein the process is carried out in a cylindrical reactor having a vertical longitudinal axis,
    having a multiplicity of Field tubes which are oriented parallel to the longitudinal axis of the reactor and welded into a tube plate at the upper end of the reactor,
    having a tube insert open at both ends which envelops the Field tubes and at its lower end projects beyond said tubes,
    having an inlet nozzle or a plurality of inlet nozzles at the bottom of the reactor for injecting a reactant mixture comprising the $C_6$-$C_{20}$-olefin, the synthesis gas and optionally the transition metal catalyst, wherein
    the Field tubes are configured in terms of their number and their dimensions such that
    the total heat transfer area of said tubes per unit internal volume of the reactor is in the range from 1 m$^2$/m$^3$ to 12 m$^2$/m$^3$ and
    the cross sectional area occupied by the Field tubes per unit cross sectional area of the tube insert is in the range from 0.03 m$^2$/m$^2$ to 0.30 m$^2$/m$^2$.

The following intimations concerning suitable and preferred configurations of the cylindrical reactor according to the invention apply correspondingly to the reactor employed in the process according to the invention for producing $C_7$-$C_{21}$-oxo products.

The term $C_7$-$C_{21}$-oxo products describes the $C_7$-$C_{21}$-aldehydes and $C_7$-$C_{21}$-alcohols obtained from the hydroformylation (oxo reaction) of $C_6$-$C_{20}$-olefins.

In the context of the present invention the internal volume of the reactor is to be understood as meaning the entire reactor volume including the volume of the internals present in the reactor. The internal volume is accordingly larger than the reaction volume, i.e. the volume of the reactor that may theoretically be filled with a reaction medium.

The reactor according to the invention combines the known principle of a loop reactor with internal recirculation of the reaction mixture driven by feeding of the reactant mixture via one or more inlet nozzle(s) into the interior defined by a tube insert (often also referred to as a guide or circulation tube) arranged concentrically to the reactor inner shell with cooling by Field tubes arranged in the interior defined by the tube insert.

Circulation reactors are known and are described in DE 198 54 637 for example. Circulation reactors are reactors of tall cylindrical construction, i.e. having a vertical longitudinal axis, and comprise as essential installation elements a tube insert arranged concentrically to the reactor inner shell and extending essentially over the entire reactor length up to the reactor ends and one or more jet nozzles which inject the reactant mixture into the reactor interior defined by the tube insert. This forms a directed internal circulation flow with the advantages that the flow conditions are clearly defined over the entire reactor volume, i.e. the parameters flow rates, gas contents, back mixing, mixing times and dwell times which are important for the configuration of the reactor may be acquired with sufficient precision, and the reactor is accordingly immediately scalable.

In the reactor according to the invention the internal circulation flow is driven by injection of the reaction mixture via a jet nozzle disposed at the lower end of the reactor which effects a vertical bottom-to-top throughflowing of the reactor interior defined by the tube insert.

A gaseous reactant and a liquid reactant are injected into the cylindrical reactor via the inlet nozzle or via a plurality of inlet nozzles. Substreams of the gaseous reactant and/or of the liquid reactant may if desired also be fed to the reactor via at least one further injection device distinct from the inlet nozzles. The reactant may be, for example, in the form of a biphasic mixture comprising a liquid phase and a gaseous phase or in the form of a triphasic mixture comprising a gaseous phase and two not (fully) miscible liquid phases.

When the reactor is used for hydroformylation a bi- or triphasic reactant mixture comprising $C_6$-$C_{20}$-olefins as a liquid organic phase, a gaseous mixture of carbon monoxide and hydrogen (synthesis gas) and optionally an aqueous solution comprising transition metal catalyst is injected into the reactor via the inlet nozzle or a plurality of inlet nozzles. As is intimated hereinbelow the catalyst may also be preformed and injected into the reactor with the liquid organic phase.

The cylindrical reactor preferably comprises at least one inlet nozzle for injecting the reactant mixture which is a jet nozzle.

The term jet nozzle refers, as is conventional, to a tube tapering in the flow direction. Generally, a single jet nozzle arranged centrally at the bottom of the reactor is employed. However, it is also possible to employ a plurality of jet nozzles, in particular arranged at regular intervals around the reactor axis, instead of a single jet nozzle. It is advantageous to employ an ejector nozzle, i.e. a jet nozzle which utilizes the kinetic energy of a high-velocity liquid jet to aspirate and disperse one or more mixture component(s). The mixture components are, for example, selected from $C_6$-$C_{20}$-olefins, synthesis gas and aqueous transition metal catalyst solutions. On account of the high energy input an ejector nozzle generates high turbulences and large shearing forces, thereby achieving very good commixing.

It is advantageously possible to employ as the jet nozzle a nozzle with an adjustable flow cross section as is described in DE 101 26 363 which makes it possible to ensure that high entry velocities for the reactant mixture into the reactor of 10 to 80 m/s, in particular of 50 to 70 m/s, may be maintained without additional external circulation pumps even under varying loads.

Contemplated substrates for the hydroformylation process according to the invention include in principle all compounds comprising one or more ethylenically unsaturated double bond(s). The process according to the invention is advantageously suitable for hydroformylation of olefins or olefin mixtures having at least 6 carbon atoms per molecule. Preference is given to employing a $C_6$-$C_{20}$-olefin or a mixture of $C_6$-$C_{20}$-olefins. One specific implementation employs a $C_8$-$C_{16}$-olefin or a mixture of $C_8$-$C_{16}$-olefins.

Among these are included, for example, olefins such as α-olefins, internal straight-chain and internal branched olefins. Suitable α-olefins are, for example, 1-hexene, 1-heptene, 1-octene, 1-nonene, 1-decene, 1-undecene, 1-dodecene, etc.

Suitable straight-chain olefins having internal double bonds are, for example, 2-hexene, 3-hexene, 2-heptene, 3-heptene, 2-octene, 3-octene, 4-octene, etc.

Suitable branched olefins having internal double bonds are, for example, 2-methyl-2-pentene, 3-methyl-2-pentene, branched heptene mixtures having internal double bonds, branched octene mixtures having internal double bonds, branched nonene mixtures having internal double bonds, branched undecene mixtures having internal double bonds, branched undecene mixtures having internal double bonds, branched dodecene mixtures having internal double bonds, etc.

The process according to the invention is suitable in particular for the hydroformylation of isomeric olefin mixtures produced by oligomerization of lower olefins, such as propene and butene. Typical oligomers suitable as starting products for the present process include, inter alia, di-, tri- and tetrapropene, di-, tri- and tetrabutene and mixed oligomers of propenes and butenes. The oligomers of butenes are obtainable on a large industrial scale by known oligomerization processes, for example by the Hüls Octal® process and the IFP Dimersol™ process. The process according to the invention furthermore allows for hydroformylation of linear long-chain olefins having a terminal double bond, obtainable by the SHOP® process or Ziegler process for example, or linear long-chain olefins having an internal double bond. Suitable starting products for the present process also include the lightly branched oligomers as are obtained by the process described in WO 95/14647. Said process comprises oligomerizing unbranched $C_2$-$C_6$ olefins over a catalyst comprising as active constituents 10 to 70 wt % nickel oxide, calculated as NiO, 5 to 30 wt % titanium dioxide and/or zirconium dioxide, 0 to 20 wt % aluminum oxide, 20 to 40 wt % silicon dioxide and 0.01 to 1 wt % of an alkali metal oxide.

So-called synthesis gas, i.e. a mixture of carbon monoxide and hydrogen, is employed as a further reactant for the process according to the invention. The composition of the synthesis gas used may be varied within wide limits.

It is preferable when the molar ratio of carbon monoxide to hydrogen is about 10:1 to 1:10, in particular 2.5:1 to 1:2.5. One preferred ratio is about 4:6.

The process according to the invention is performed under homogeneous catalysis. To this end, a suitable catalyst or catalyst precursor is generally introduced into the reactor with the olefin and the synthesis gas. The catalysts or catalyst precursors preferably comprise a metal of group VIII B of the periodic table, particularly preferably cobalt or rhodium, in particular cobalt. It is preferable to employ a metal carbonyl complex catalyst, specifically a cobalt carbonyl complex catalyst, homogeneously dissolved in the reaction medium. Provided that the catalytically active species itself is not fed to the reactor the hydroformylation conditions generally form catalytically active species from the particular catalyst precursors employed, said species generally being transition metal carbonyl or transition metal carbonyl hydride compounds.

Suitable cobalt catalyst precursors are, for example, cobalt(II) chloride, cobalt(II) sulfate, cobalt(II) carbonate, cobalt(II) nitrate, the amine or hydrate complexes thereof or cobalt carboxylates, for example cobalt(II) formate, cobalt (II) acetate or cobalt(II) ethylhexanoate. Also suitable are cobalt complexes, in particular cobalt carbonyls or cobalt carbonyl hydrides.

Suitable rhodium catalyst precursors or complexes are, for example, rhodium(II) and rhodium(III) salts, such as rhodium(III) chloride, rhodium(III) nitrate, rhodium(III) sulfate, potassium rhodium sulfate, rhodium(II)/rhodium(III) carboxylate, rhodium(II) and rhodium(III) acetate, rhodium (III) oxide, salts of rhodium(III) acid, trisammonium hexachlororhodate(III) etc. Also suitable are rhodium complexes, such as rhodium biscarbonylacetylacetonate, acetylacetonatobisethylene rhodium(I) etc. Preference is given to employing rhodium biscarbonylacetylacetonate or rhodium acetate as the catalyst precursor compound.

The catalyst or its precursor compound may be fed to the reactor in dissolved form in the starting olefin, in an organic solvent, in water or in a mixture thereof. In one specific implementation the catalyst is preformed before it is injected into the reactor. This may be achieved, for example, by bringing an aqueous cobalt(II) salt solution into contact with synthesis gas to form a hydroformylation-active cobalt catalyst. The aqueous solution comprising the cobalt catalyst may be brought into contact with the starting olefin and/or the external organic solvent simultaneously or subsequently, thus extracting the cobalt catalyst into the organic phase. Said phase is then fed to the reactor.

The reaction is performed in the liquid phase and the reaction mixture comprises unconverted olefins, dissolved synthesis gas, the homogeneously dissolved hydroformylation catalyst, at least one aldehyde as the hydroformylation product and possibly byproducts of the hydroformylation reaction. Byproducts of the oxo reaction are, for example, the products of the aldol reaction of the aldehydes formed. Suitable external organic solvents are inert hydrocarbons, such as paraffin fractions, aromatic hydrocarbons, such as benzene, toluene or xylene. However, it is preferable when the aldehydes and/or alcohols formed in the hydroformylation and the high-boiling byproducts of the hydroformylation serve as solvent.

The temperature during the hydroformylation is generally 100° C. to 250° C., in particular 145° C. to 200° C. The hydroformylation is preferably carried out at a pressure in the range from 10 to 400 bar, particularly preferably 20 to 350 bar, in particular 100 to 300 bar.

The heat of reaction is removed by indirect heat exchange inside the reactor via Field tubes arranged inside the reactor interior bounded by the tube insert. In the context of the invention the term Field tubes (or boiler tubes) is used to describe double-walled tubes having an inner tube open at both ends through which the cooling liquid is passed from top to bottom, said liquid undergoing partial evaporation in the interspace between the inner tube open at the bottom and the outer tube closed at the bottom and being withdrawn as a steam/water mixture at the upper end of said tube. The heat generated by the exothermic reaction is thus withdrawn from the reaction mixture. Customary liquids or gases may be employed as the coolant therefor. It is preferable when the coolant employed is water, for example softened and degassed water (so-called boiler feed water).

In accordance with the invention the Field tubes are configured such that they have a sufficient total heat transfer area to ensure that the heat of the highly exothermic reaction is removed sufficiently rapidly but that they simultaneously occupy the cross sectional area of the tube insert only to an extent where the internal circulation flow is not excessively impeded and no fluid dynamic constriction (cage effect) in the tube insert occurs.

The total heat transfer area is presently to be understood as meaning the sum of the heat transfer areas of all Field tubes to the extent that they are in contact with the reaction mixture. In accordance with the invention the total heat transfer area of the Field tubes per unit internal volume of the reactor is in the range from 1 $m^2/m^3$ to 12 $m^2/m^3$. It is preferable when the total heat transfer area of the Field tubes per unit internal volume of the reactor is in the range from 7 to 11 $m^2/m^3$. In accordance with the invention the Field tubes are configured such that they withstand the reaction conditions prevailing in the reactor. When the reactor is used for hydroformylation the Field tubes are configured such that they withstand the pressures of up to about 400 bar and the temperatures of up to about 250° C. prevailing in the reactor. Important design features of the Field tubes are their internal diameter, wall thickness, number and length. The constructional configuration of said tubes takes into account the reaction conditions and the known values for the exothermicity and kinetics of the hydroformylation reaction according to the engineering knowledge familiar to those skilled in the art.

A further inventive design feature of the Field tubes is that the cross sectional area occupied thereby per unit cross sectional area of the tube insert is in the range from 0.03 $m^2/m^2$ to 0.30 $m^2/m^2$. It is preferable when the cross sectional area occupied by the Field tubes per unit cross sectional area of the tube insert is in the range from 0.07 $m^2/m^2$ to 0.25 $m^2/m^2$. The specified cross sectional area refers to the entire cross sectional area of the tube insert, i.e. the wall thickness of the tube insert is not deducted.

Although it is necessary for the Field tubes to provide sufficient heat transfer area for the heat of reaction of the highly exothermic hydroformylation to be removed effectively, the above condition ensures that the number of Field tubes in the tube insert is not sufficient to bring about a fluid dynamic constriction (cage effect) that would result in a nonuniform velocity distribution of the liquid in the tube insert. This would bring about an unequal distribution of the gas fraction in the liquid and could influence the internal circulation to the effect that the volume flow rate is reduced/a backflow forms at the periphery of the tube insert. This would in turn result in fewer gas bubbles being entrained, thus allowing the carbon monoxide partial pressure, in particular in the annular space outside the tube insert, to reach values low enough for undesired precipitation of metallic cobalt to occur.

The cross sectional area of the tube insert per unit cross sectional area of the reactor (1) is preferably 0.60 $m^2/m^2$ to 0.75 $m^2/m^2$, particularly preferably 0.66 $m^2/m^2$ to 0.72 $m^2/m^2$. The specified cross sectional areas refer to the total cross sectional area of the tube insert (i.e. including the wall thickness) and to the cross sectional area of the reactor resulting from its internal diameter (i.e. excluding the wall thickness).

The Field tubes are affixed in the upper region of the reactor. Affixing may be effected in customary fashion, for example by welding. This affixing may be effected at the lid of the reactor for example. The devices for feeding and discharging the coolant which flows through the Field tubes are typically integrated into the reactor head. To this end the reactor head may comprise, for example, two separate compartments, wherein one is provided with the inlet for the coolant and distributes the coolant into the Field tubes and the other receives the heated coolant flowing out of the Field tubes, said coolant then exiting the reactor head through an outlet. The various parts forming the reactor head may be joined together by welding, adhesive joins, riveting and screw connection. In one preferred implementation the various parts forming the reactor head are joined together by screw connection.

Further holding devices may be provided to hold the Field tubes in the desired geometric arrangement in the interior of the reactor. In the region of the tube insert these holding devices are, for example, attached to the inner wall of the tube insert. Suitable holding devices are in particular gratings through which the Field tubes are passed. These holding devices have cross sectional areas unoccupied by Field tubes for the flowing reaction medium. One or, if present, more, or all present holding devices may comprise additional flow internals which can assume the function of mixing elements. Thus a holding device provided with mixing elements may simultaneously act as a static mixer. For example a holding device in the form of a grating through which the Field tubes are passed may comprise additional bars, thus additionally assuming the function of a static mixer.

In a preferred implementation the cylindrical reactor according to the invention comprises a plurality of holding devices. It is preferable when at least one holding device is configured as a static mixer in the lower half of the reactor. In one particularly preferred configuration the lowest (nearest to the inlet nozzle(s)) holding device is configured as a static mixer.

Since the Field tubes have a coolant flowing through them they can exhibit a marked temperature difference compared to the reaction medium and the holding device(s). Temperature variations between the coolant and the reaction medium cannot be ruled out either. The Field tubes are therefore disposed movably, i.e. not fixedly but rather via one or more bearings, in the holding device. This makes it possible to avoid material stress and consequent damage due to different levels of thermal expansion.

To limit mobility the Field tubes may have protuberances on their outer walls above and/or below a holding device. The protuberances are preferably uniformly distributed over the circumference of the outer wall, at the same height in each case. It is particularly preferable when the protuberances are arranged in respective pairs above and below a holding device. For example, two, three, four, five or six pairs are distributed along the circumference. These protuberances are preferably attached externally to the outer wall of the Field tubes by means of an atomic-level join, for example by welding, soldering, adhesive bonding. The holding device may moreover rest on the protuberances of the Field tubes. Since the holding device is affixed to the inner wall of the tube insert the protuberances may thus also serve to secure the tube insert.

Affixing of the holding devices to the inner wall of the tube insert may be effected in customary fashion by means of an atomic-level join, for example by welding, soldering, adhesive bonding, in particular by welding.

Further guiding devices are provided to hold the tube insert in the desired geometric arrangement in the interior of the reactor. The guiding of the tube insert at the inner wall of the cylindrical reactor may be effected via spacers or rollers in the annular space. This makes it possible to compensate for temperature-dependent dimensional changes.

The guiding devices may be affixed to the outer wall of the tube insert or to the reactor inner wall. They are preferably affixed to the outside of the tube insert. Said devices are distributed over the circumference of the annular space in accordance with the tube arrangement. The guiding devices are preferably distributed uniformly over the circumference of the annular space. They form, for example, an equilateral triangle, a regular hexagon, a square, a regular octagon. The guiding devices are preferably disposed at the same height as a holding device.

The reactor according to the invention further preferably comprises a gas distributor which is particularly preferably a gas distributor ring. In one preferred configuration the reactor according to the invention comprises a gas distributor ring at the lower end of the tube insert, in particular at its inner wall. A substream of the gaseous component of the reactant mixture may be fed to the reactor via the gas distributor ring. When the reactor according to the invention is used for hydroformylation a substream of the synthesis gas may be supplied thereto via the gas distributor ring. If such a substream is employed the substream preferably amounts to 1 to 20%, particularly preferably 2 to 15%, of the entire gas stream fed to the reactor.

Providing an additional gas distributor ensures a markedly improved radial distribution of gas and liquid and thus a markedly increased internal circulation stream. This brings about a bottom-to-top flow along the inner wall of the tube insert which supports the loop flow around the tube insert.

The reactor according to the invention preferably comprises a static mixer or a plurality of static mixers arranged in the tube insert. This improves the radial distribution of the reaction mixture in the tube insert. As described hereinabove the holding devices may additionally assume the function of a static mixer. It is preferable when individual Field tube holding gratings of the Field tube holding gratings present are used as static mixers in which the number of bars used for holding the Field tubes is maximized, i.e. is as large as possible. This reduces the free cross section of holding gratings thus configured. Increasing the pressure drop results in additional turbulence and thus in improved gas and liquid distribution. This deliberate generation of pressure drop and turbulence in the tube insert additionally dissipates energy.

The tube insert open at both ends which envelops the Field tubes and at the lower end projects beyond said tubes preferably extends as far as possible toward the upper end of the reactor so as to avoid dead zones in the upper region to the greatest possible extent. However, an excessive pressure drop should be avoided. It has proven to be particularly advantageous when the tube insert envelops the Field tubes to an extent of 80% of the length thereof, preferably to an extent of 90% of the length thereof.

A further improvement in commixing may be achieved by providing, above the tube insert and perpendicularly thereto, a baffle plate through which the Field tubes are passed. The baffle plate is preferably disk-shaped and has a diameter of at least half the diameter of the tube insert and less than the internal diameter of the reactor. The thickness of the baffle plate is chosen such that it mechanically withstands the flow pressure. The thickness of the baffle plate is preferably in the range from 5 to 10 mm.

A further improvement in commixing in the reactor according to the invention may be achieved when the reactor ends are curved. It is particularly advantageous for the bottom of the reactor to be curved. Specifically, it is particularly preferable when the bottom is curved on the inside.

Discharging of the reaction mixture is effected biphasically via the lid of the reactor. When a baffle plate is employed discharging of the reaction mixture is effected above the baffle plate.

Workup of the liquid reaction effluent comprising at least an aldehyde as the hydroformylation product, unconverted olefins, dissolved synthesis gas, the homogeneously dissolved hydroformylation catalyst and any byproducts of the hydroformylation reaction is effected according to customary processes known to those skilled in the art. For instance, WO 01/14297 describes a continuous process for hydroformylation of olefins having 6 to 20 carbon atoms. This document describes in detail how a hydroformylation reaction effluent may be worked-up with an unmodified cobalt catalyst and specifically how the cobalt catalyst may be recycled into the reaction essentially without catalyst losses.

The invention is more particularly elucidated hereinbelow by reference to figures and exemplary embodiments.

Figure 1:
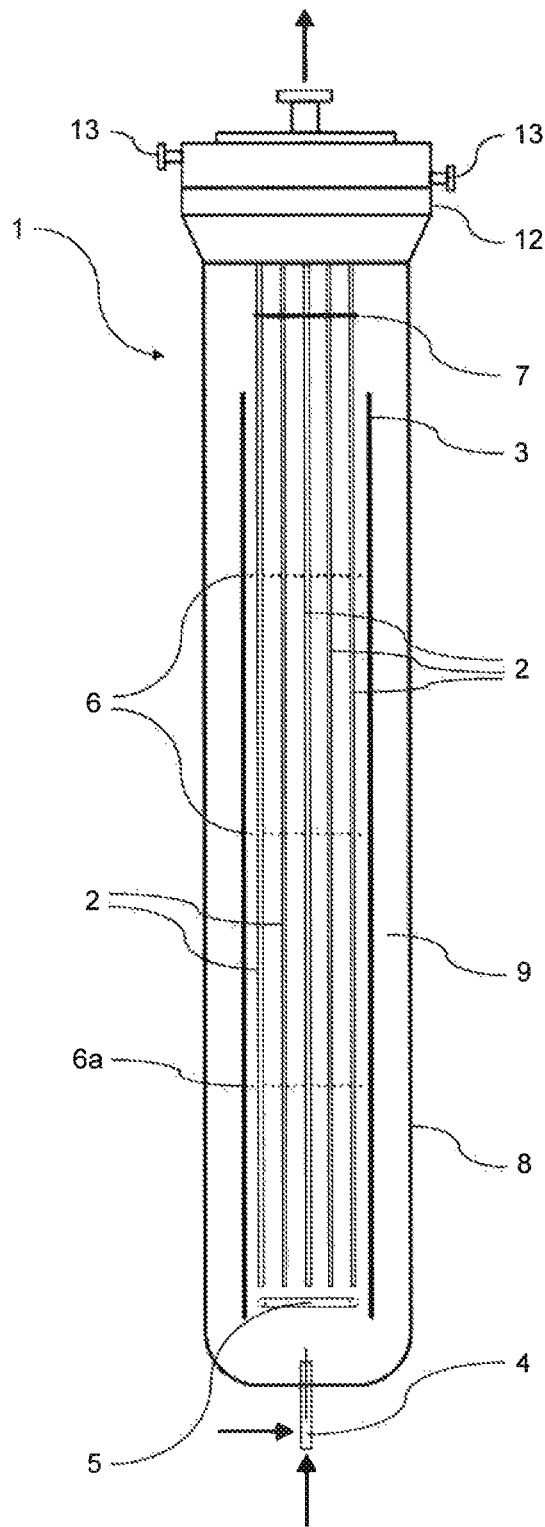
FIG. 1 shows a longitudinal section through a preferred embodiment of a reactor according to the invention.

In the figures identical reference numerals describe respective identical or corresponding features.
1 reactor
2 Field tubes
3 tube insert
4 inlet nozzle
5 gas distributor ring
6 holding device
6a holding device and static mixer
7 baffle plate
8 reactor shell
9 annular space
10 outer tube
11 inner tube
12 reactor head
13 lifting lugs
14 protuberances
15 spacers The longitudinal section in FIG. 1 shows a schematic view of a preferred cylindrical reactor 1 having a vertical longitudinal axis having a multiplicity of Field tubes 2 and a reactor head 12 shown in schematic form. The Field tubes 2 are welded into a tube plate at the upper end of the reactor 1 which in the present case forms the lower end of the reactor head 12. Arranged coaxially in the reactor 1 is a tube insert 3 open at both ends which envelops the Field tubes 2 and at its lower end projects beyond said tubes. The reactor head comprises, inter alia, parts of the coolant circuit for distributing the inflowing cold coolant to the individual Field tubes 2 and for discharging the heated coolant exiting the individual Field tubes 2 and the vapor formed (not shown). The reactor head 12 further comprises the outlet for the reaction mixture, it being possible to discharge gaseous and liquid components together. Feeding of the reactants is effected via an inlet nozzle 4 at the lower end of the reactor 1. The inlet nozzle 4 is configured as an ejector nozzle by means of which the $C_6$-$C_{20}$-olefins and the synthesis gas are simultaneously fed. If desired, aqueous transition metal catalyst, in particular the metal carbonyl complex catalyst, may additionally be fed to nozzle 4 with one of the streams. A substream of the synthesis gas may be fed via a gas distributor ring 5 at the lower end of the tube insert 3. By way of example, a holding device configured as static mixer 6a and two further holding devices 6 are depicted in the tube insert 3. Disposed above the tube insert 3 is a baffle plate 7 arranged perpendicularly to the tube insert 3.

Figure 2:
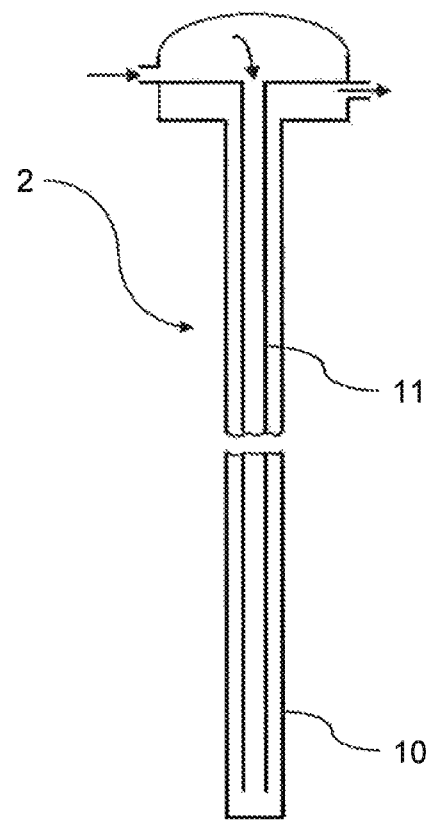
FIG. 2 shows a longitudinal section through an individual Field tube.

By way of example, FIG. 2 shows a schematic view of an individual Field tube 2 which is in each case composed of a sleeve, referred to here and in what follows as outer tube 10, and a coaxial inner tube 11. The outer tube 10 is closed at its lower end while the coaxial inner tube 11 is open at its lower end. In the embodiment depicted coolant, for example water, in particular boiler feed water, may be introduced into the inner tube 11 from above and withdrawn at the upper end of the outer tube 10 as heated coolant, for example as a vapor-liquid mixture. The coolant is typically passed downward through the inner tube and passed upward between the inner tube 11 and the outer tube 10. However, the coolant flow may alternatively be reversed. The feed and discharge for the coolant which flows through the Field tubes 2 are typically integrated into the reactor head 12. To this end the reactor head 12 may comprise, for example, two separate compartments, wherein one is provided with the inlet for the coolant and distributes the coolant into the Field tubes 2 and the other receives the heated coolant flowing out of the Field tubes 2, said coolant then exiting the reactor head 12 through an outlet.

Figure 2A:
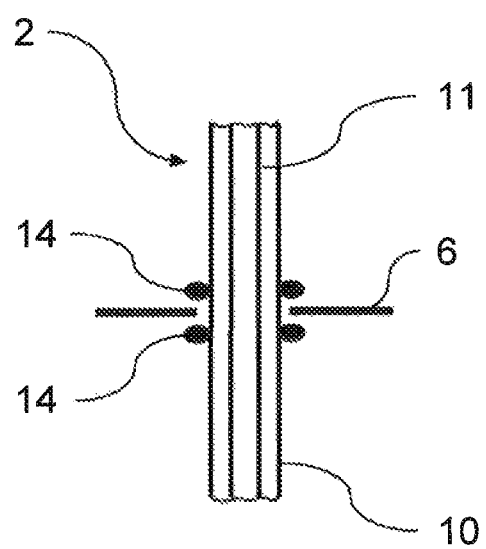
FIG. 2a shows a detailed view of an individual Field tube in a holding device with protuberances attached to the outer wall of the Field tube above and below the holding device.

FIG. 2a shows a detailed view of an individual Field tube 2 in a holding device 6. Attached to the outer wall of the Field tube 2 above and below the holding device 6 are protuberances which form a bearing for the holding device 6.

Figure 3:
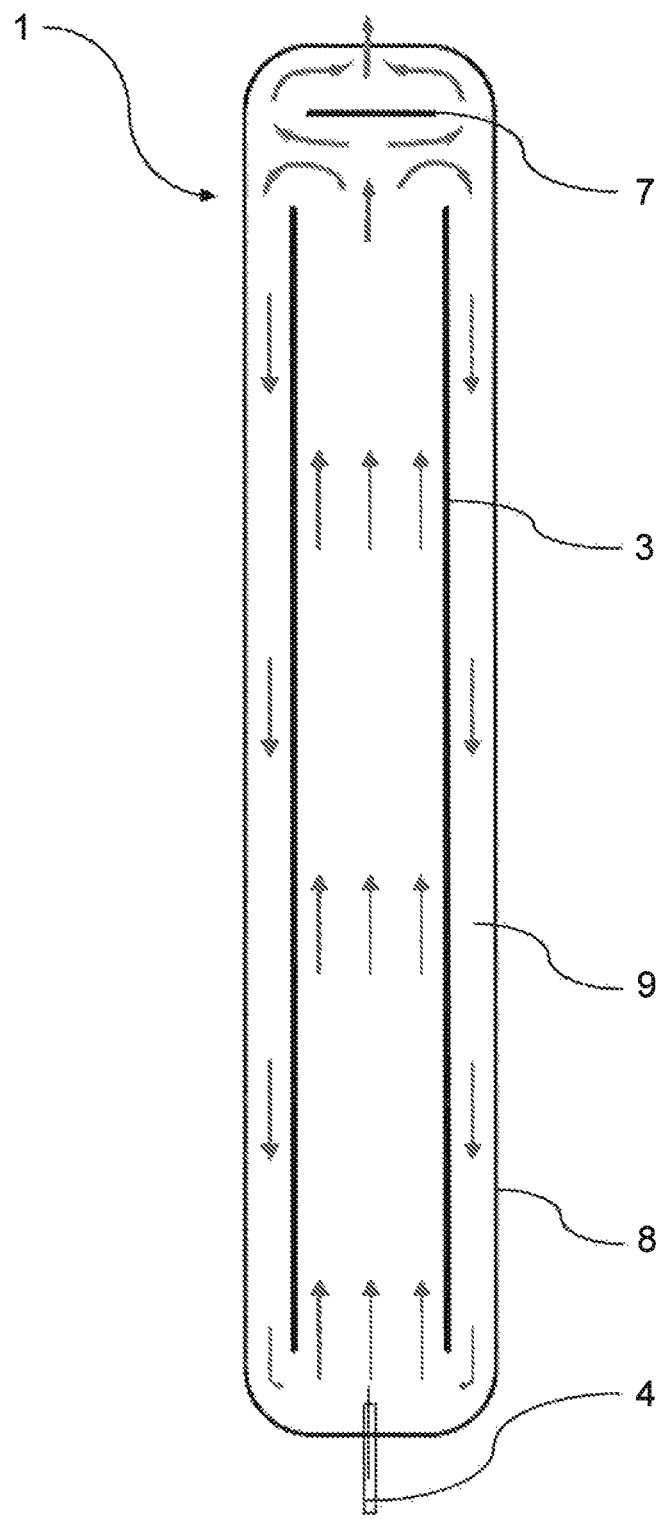
FIG. 3 shows a schematic view of the liquid flow through the embodiment depicted in FIG. 1.

FIG. 3 illustrates the liquid flow in the reactor 1 depicted in FIG. 1. This liquid flow is depicted schematically with arrows. Inside the tube insert 3 an upward flow is induced by the jet nozzle 4. The baffle plate 7 deflects the flow to provide a downward flow in annular space 9 between the reactor inner wall and the tube insert 3.

Figure 4:
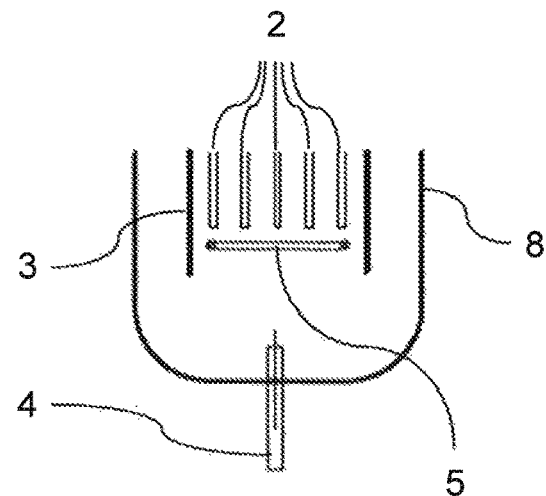
FIG. 4 shows a detailed drawing of the lower reactor region in the configuration having a gas distributor ring.

FIG. 4 shows a detailed drawing of the lower reactor region of an embodiment according to the invention. This shows the reactor 1 comprising a jet nozzle 4 for injecting the reactant mixture. A substream of the synthesis gas may be fed to the reactor 1 via a gas distributor ring 5 at the lower end of the tube insert 3.

Figure 5:
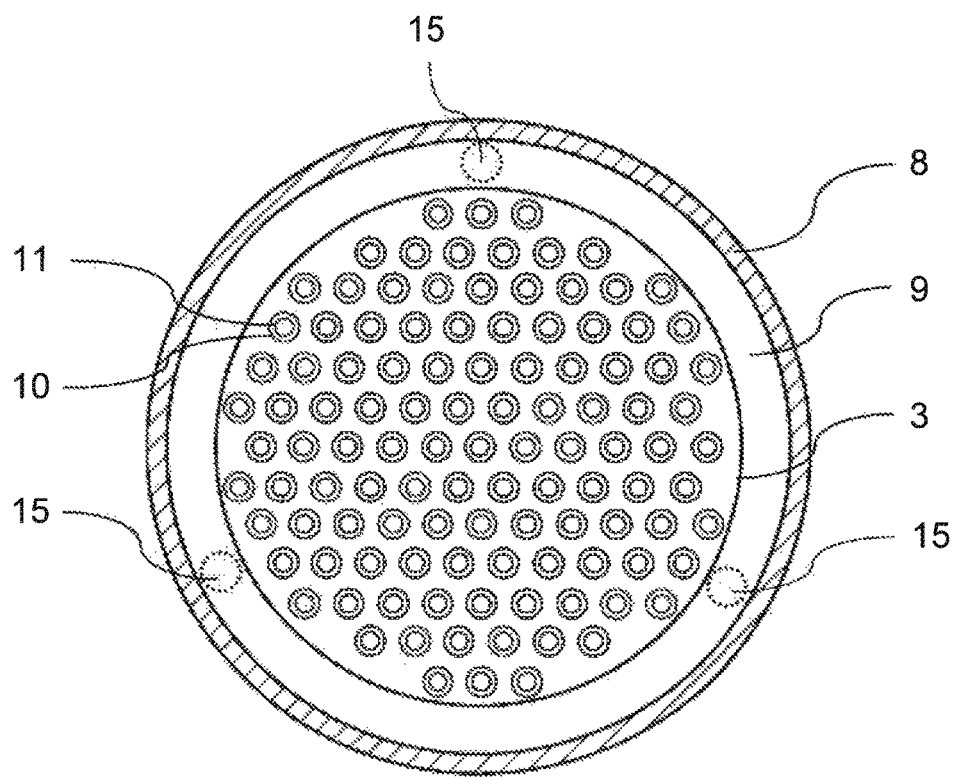
FIG. 5 shows a cross section through a reactor depicted in FIG. 1.

FIG. 5 shows a cross section through the reactor shown in FIG. 1 at a point where no holding device is present. This cross section is referred to here and in what follows as a tubesheet. The tubesheet shows the number, relative dimensions and arrangement inside the tube insert 3 of the Field tubes each composed of an outer tube 10 and a coaxial inner tube 11. The figure depicts a possible equilateral triangular arrangement of the Field tubes in the tube insert 3 also known as a staggered tube arrangement. A square arrangement of the Field tubes in the tube insert also known as an aligned tube arrangement would likewise be suitable.

The tube insert 3 is arranged coaxially with the reactor shell 8 and envelops the Field tubes each composed of an outer tube 10 and a coaxial inner tube 11. Disposed between the reactor shell 8 and the tube insert is an annular space 9. The spacers 15 are distributed over the circumference of the annular space 9 in accordance with the tube arrangement. In the present case said spacers form an equilateral triangle though a regular hexagonal arrangement or, in the case of an aligned arrangement, a square arrangement would also be suitable. The spacers 15 are here intended to be merely implied since they are preferably disposed at the same height as a holding device.

EXAMPLES

Example 1

A hydroformylation plant comprising a main reactor and a postreactor is employed. The main reactor is 18.0 m in length and has an internal diameter of 1.0 m. The upper tube plate which is simultaneously the lid of the reactor is fitted with 64 Field tubes having an external diameter of 30.0 mm. A tube insert having an internal diameter of 0.84 m is disposed in the main reactor. The reactants (isooctene and synthesis gas comprising 40 vol % carbon monoxide and 60 vol % hydrogen) and the aqueous cobalt acetate solution are introduced via a nozzle at the bottom of the reactor. The main reactor is operated at 187° C. and 275 bar. The temperature in the postreactor is at the same level but the pressure is held at 3 bar below the pressure in the main reactor. 1 t/h of synthesis gas and 3 t/h of isooctene produced as per WO 95/14647 were employed.

The ratio of the total heat transfer area of the Field tubes per unit internal volume of the main reactor is 9.4 $m^2/m^3$. The cross sectional area occupied by the Field tubes per unit cross sectional area of the tube insert is 0.08 $m^2/m^2$.

Isononanol is produced in this hydroformylation plant. In order to compensate for losses due to cobalt deposited in the reactor it is necessary to supplement 160 kg of cobalt as cobalt acetate solution over the course of one year. This corresponds to 0.01 kg of cobalt per ton of product.

This reactor was operated for five years before the cobalt deposits were removed using dilute nitric acid (see international patent application WO2015/018 710).

Comparative Example

The plant and the operating conditions are identical to those in inventive example 1. However, in departure therefrom the main reactor is fitted with 158 Field tubes having an external diameter of 48.3 mm and the tube insert has an internal diameter of 1.23 m.

The ratio of the total heat transfer area of the Field tubes per unit internal volume of the reactor is 16.1 $m^2/m^3$. The cross sectional area occupied by the Field tubes per unit cross sectional area of the tube insert is 0.25 $m^2/m^2$.

In this hydroformylation plant isononanol is likewise produced from isooctene and synthesis gas comprising 40 vol % carbon monoxide and 60 vol % hydrogen with the aid of a cobalt catalyst. The main reactor is operated at 187° C. and 275 bar. The temperature in the postreactor is at the same level but the pressure is held at 3 bar below the pressure in the main reactor. 1 t/h of synthesis gas and 3 t/h of isooctene produced as per WO 95/14647 were employed.

Over the course of one year it is necessary to supplement 5000 kg of cobalt as cobalt acetate solution to compensate the losses due to cobalt deposited in the reactor. This corresponds to 0.06 kg of cobalt per ton of product; the cobalt losses are thus markedly higher compared to the inventive example.

Blockages in the pipes occurred after approximately one year and the cobalt deposits had to be removed using dilute nitric acid to remove the blockage.

The invention claimed is:

1. A cylindrical reactor (1) having a vertical longitudinal axis,
   having a multiplicity of Field tubes (2) which are oriented parallel to the longitudinal axis of the reactor (1) and affixed to the upper end of the reactor (1),
   having a tube insert (3) open at both ends which envelops the Field tubes (2) and at its lower end projects beyond said tubes,
   having an inlet nozzle (4) or a plurality of inlet nozzles (4) at the bottom of the reactor (1) for injecting a reactant mixture comprising at least one gaseous component and at least one liquid component, wherein
   the Field tubes (2) are configured in terms of their number and their dimensions such that
   the total heat transfer area of said tubes per unit internal volume of the reactor is in the range from 1 $m^2/m^3$ to 12 $m^2/m^3$ and
   the cross sectional area occupied by the Field tubes (2) per unit cross sectional area of the tube insert (3) is in the range from 0.03 $m^2/m^2$ to 0.30 $m^2/m^2$.

2. The cylindrical reactor (1) according to claim 1, wherein the cross sectional area of the tube insert (3) per unit cross sectional area of the reactor (1) is 0.60 $m^2/m^2$ to 0.75 $m^2/m^2$, preferably 0.66 $m^2/m^2$ to 0.72 $m^2/m^2$.

3. The cylindrical reactor (1) according to claim 1, wherein said reactor comprises a gas distributor ring (5) at the lower end of the tube insert (3) at the inner wall thereof via which a substream of the gaseous component of the reactant mixture is fed.

4. The cylindrical reactor (1) according to claim 1, wherein said reactor comprises a holding device (6) or a plurality of holding devices (6) in the tube insert (3).

5. The cylindrical reactor (1) according to claim 1, wherein said reactor comprises a static mixer (6a) or a plurality of static mixers (6a) in the tube insert (3).

6. The cylindrical reactor (1) according to claim 4, wherein one or more of the holding devices (6) additionally function as static mixers.

7. The cylindrical reactor (1) according to claim 1, wherein the Field tubes (2) are configured in terms of their number and their dimensions such that
   the total heat transfer area of said tubes per unit internal volume of the reactor is in the range from 7 $m^2/m^3$ to 11 $m^2/m^3$ and
   the cross sectional area occupied by the Field tubes (2) per unit cross sectional area of the tube insert (3) is in the range from 0.07 $m^2/m^2$ to 0.25 $m^2/m^2$.

8. The cylindrical reactor (1) according to claim 1, wherein the tube insert (3) envelops the Field tubes (2) to an extent of 80% of the length thereof, preferably to an extent of 90% of the length thereof.

9. The cylindrical reactor (1) according to claim 1, wherein said reactor comprises a baffle plate (7) above the tube insert (3).

10. A continuous process for producing $C_7$-$C_{21}$-oxo products by hydroformylation of at least one $C_6$-$C_{20}$-olefin with synthesis gas in the presence of a homogeneously dissolved transition metal catalyst, wherein the process is carried out in a cylindrical reactor (1) having a vertical longitudinal axis, having a multiplicity of Field tubes (2) which are oriented parallel to the longitudinal axis of the reactor (1) and welded into a tube plate at the upper end of the reactor (1), having a tube insert (3) open at both ends which envelops the Field tubes (2) and at its lower end projects beyond said tubes, having an inlet nozzle (4) or a plurality of inlet nozzles (4) at the bottom of the reactor (1) for injecting a reactant mixture comprising the $C_6$-$C_{20}$-olefin, the synthesis gas and optionally the transition metal catalyst, wherein the Field tubes (2) are configured in terms of their number and their dimensions such that the total heat transfer area of said tubes per unit internal volume of the reactor is in the range from $1 \text{ m}^2/\text{m}^3$ to $12 \text{ m}^2/\text{m}^3$ and the cross sectional area occupied by the Field tubes (2) per unit cross sectional area of the tube insert (3) is in the range from $0.03 \text{ m}^2/\text{m}^2$ to $0.30 \text{ m}^2/\text{m}^2$.

11. The process according to claim 10, wherein the transition metal catalyst is a metal carbonyl complex catalyst, preferably a cobalt carbonyl complex catalyst.

\* \* \* \* \*